United States Patent
Williams et al.

(10) Patent No.: US 10,799,483 B2
(45) Date of Patent: Oct. 13, 2020

(54) USE OF ISOXAZOLINE COMPOUNDS FOR TREATING DEMODICOSIS

(71) Applicant: Intervet Inc., Madison, NJ (US)

(72) Inventors: Heike Williams, Offenbach am Main (DE); Anja Regina Heckeroth, Stadecken-Elsheim (DE); Janina Tanzler, Nieder-Olm (DE); Regis Joel Alain Frenais, Meignanne (FR)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/944,967

(22) Filed: Apr. 4, 2018

(65) Prior Publication Data

US 2018/0318265 A1    Nov. 8, 2018

Related U.S. Application Data

(63) Continuation of application No. 15/537,547, filed as application No. PCT/EP2015/080744 on Dec. 21, 2015, now abandoned.

(30) Foreign Application Priority Data

Dec. 22, 2014 (EP) ..................... 14199562

(51) Int. Cl.
*A61K 31/42* (2006.01)
*A61K 31/422* (2006.01)
*A61K 9/00* (2006.01)
*A61K 9/20* (2006.01)

(52) U.S. Cl.
CPC ............ *A61K 31/42* (2013.01); *A61K 9/0014* (2013.01); *A61K 9/0019* (2013.01); *A61K 9/0053* (2013.01); *A61K 9/0056* (2013.01); *A61K 9/20* (2013.01); *A61K 31/422* (2013.01)

(58) Field of Classification Search
CPC .... A61K 31/42; A61K 31/422; A61K 9/0014; A61K 9/0019; A61K 9/0053; A61K 9/0056; A61K 9/20
See application file for complete search history.

(56) References Cited

U.S. PATENT DOCUMENTS

| | | |
|---|---|---|
| 2007/0066617 A1 | 3/2007 | Mita et al. |
| 2012/0232026 A1 | 9/2012 | Curtis et al. |
| 2013/0065846 A1 | 3/2013 | Soll et al. |
| 2013/0203692 A1 | 8/2013 | Soll et al. |

FOREIGN PATENT DOCUMENTS

| | | |
|---|---|---|
| JP | 2014508773 A | 4/2014 |
| JP | 2014527081 A | 10/2014 |
| RU | 2067863 C1 | 10/1996 |
| WO | 2005085216 | 9/2005 |
| WO | 2007079162 | 7/2007 |
| WO | 2009002809 | 12/2008 |
| WO | 2009003075 A1 | 12/2008 |
| WO | 2009024541 | 2/2009 |
| WO | 2009080250 | 7/2009 |
| WO | 2010070068 | 6/2010 |
| WO | 2010079077 | 7/2010 |
| WO | 2012120399 A1 | 9/2012 |
| WO | 2013039948 A1 | 3/2013 |
| WO | 2013119442 | 8/2013 |
| WO | 2013150052 | 10/2013 |
| WO | 2013150055 | 10/2013 |
| WO | 2015091898 A1 | 6/2015 |

OTHER PUBLICATIONS

Fourie, Josephus et al., Efficacy of orally administered fluralaner (BravwectoTM) or topical applied imidacloprid/moxidectin (Advocate?) against generalized demodicosis in dogs, Parasites & Vectors, Mar. 28, 2015, pp. 187, vol. 8 No. 1.
International Search report for PCTEP2015080744 dated Feb. 19, 2016, 5 pages.
Beugnet, Frederic, et al., Efficacy of oral afoxolaner for the treatment of canine generalised demodicosis, Parasite, 2016, 23, 14.
Merck Vet. Manual, 10th Edition, 2010, C. M. Kahn, Editor, Merck & Co., Inc., Whitehouse Station, NJ USA, 840-841.
Six, Robert H. et al., Efficacy of sarolaner, a novel oral isoxazoline, against two commonmite infestations in dogs: *Demodex* spp. and Otodectes cynotis, Veterinary Parasitology 222, 2016, 62-66.
English language translation of NPL-Kolesnikova-2012-56.
Kolesnikova, N.A., Effective treatment regimens for demodicosis in dogs, VetPharma, 2012, 56-58, 2(12).
Rohdich, N et al., A randomized, blinded, controlled and multicentered field study comparing the efficacy and safety of Bravecto™ (fluralaner) against Frontline™ (fipronil) in flea- and tick-infested dogs, Parasites & Vectors, 2014, pp. 1-5, vol. 7, issue 83.
Demodex, Nanzan-do Medical Dictionary (Deluxe Edition), 1998, 1547, 18th edition. English Abstract.
Ferrer, Lluis et al., Immunology and pathogenesis of canine demodicosis, Veterinary Dermatology, 2014, 427-e65, 25.
Mook, Deborah M. et al., Use of Selamectin and Moxidectin in the Treatment of Mouse Fur Mites, Journal of the American Association for Laboratory Animal Science, 2008, 20-24, 47(3).
Schnabl, B. et al., Oral selamectin in the treatment of canine generalised demodicosis, Veterinary Record, 2010, 710-714, 166.

*Primary Examiner* — Alicia L Otton

(57) ABSTRACT

The present invention relates to methods of treating demodicosis by administering an isoxazoline compound of formula (I)

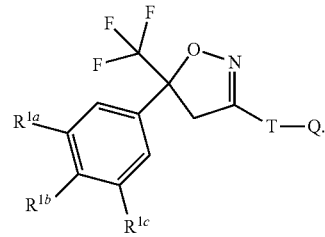

28 Claims, No Drawings

USE OF ISOXAZOLINE COMPOUNDS FOR TREATING DEMODICOSIS

CROSS-REFERENCE TO RELATED APPLICATIONS

This application is a Continuation of U.S. application Ser. No. 15/537,547, filed on Jun. 19, 2017; which is a national stage entry under 35 U.S.C. § 371 of PCT/EP2015/080744, filed on Dec. 21, 2015, which claims priority to EP Application No. EP14199562.1, filed on Dec. 22, 2014, the contents of PCT/EP2015/080744 and U.S. Ser. No. 15/537,547 are hereby incorporated by reference in their entirety.

FIELD OF INVENTION

The present invention relates to the prevention or treatment of parasitic arthropod infestations of animals.

BACKGROUND OF INVENTION

*Demodex* spp. mites are normal commensals of the skin of a number of animals parasitising within the sebaceous glands connected to the hair follicles. Should their numbers increase dramatically, they are capable of producing a disease known as demodicosis or demodectic mange.

Demodicosis is a non contagious inflammatory parasitic dermatosis caused by overpopulation of the follicular *Demodex* mites. Demodicosis can be classified as localized or generalized according to the extent of the lesions. Localized demodicosis is a benign disease and most cases resolve spontaneously within six to eight weeks.

Generalized demodicosis is a severe disease with generalized lesions that are usually aggravated by secondary bacterial infections (pyodemodicosis). Accompanying pododermatitis is common. Dogs can have systemic illness with generalized lymphadenopathy, lethargy, and fever when deep pyoderma, furunculosis, or cellulitis is seen. Diagnosis is not difficult, as deep skin scrapings or hair plucking reveal mites, eggs, and larval forms in high numbers.

Chronic generalized demodicosis is a frustrating and difficult skin disease to treat. In dogs that are otherwise healthy, the generalized form of the disease is unlikely to resolve without therapy.

Therapeutic options that are currently available include amitraz, ivermectin, milbemycin oxime, moxidectin orally and moxidectin topically, mostly to be given at multiple occasions (daily, weekly or monthly) for periods of three months or more.

To be effective, these treatment regimens require high owner compliance over an extended period of time. Owner compliance can be an important factor in treatment success when multiple doses of a treatment spread over a long period of time are required in order to achieve a satisfactory outcome.

A problem frequently encountered with the treatment of demodicosis in dogs is the inability to ensure that a dog is absolutely free from mites after treatment and re-infestation can be detected months after completion of a treatment that was initially considered to be successful.

Therefore it is desirable to provide a method to treat *Demodex* spp. infestation and demodicosis in animals, especially dogs, that effectively controls mites and is convenient to administer and therefore supports owner compliance and prevents re-infestation and relapse of the disease.

SUMMARY OF THE INVENTION

The current invention provides to use an isoxazoline compound of formula (I)

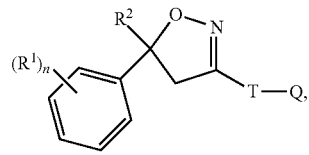

Formula (I)

wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5- or 6-membered ring, which is optionally substituted by one or more radicals Y, Y=methyl, halomethyl, halogen, CN, $NO_2$, $NH_2$—C=S, or two adjacent radicals Y form together a chain, especially a three or four membered chain;

Q=X—$NR^3R^4$ or a 5-membered N-heteroaryl ring, which is optionally substituted by one or more radicals;

X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

$R^3$-1

$R^3$-2

$R^3$-3

$R^3$-4

$R^3$-5

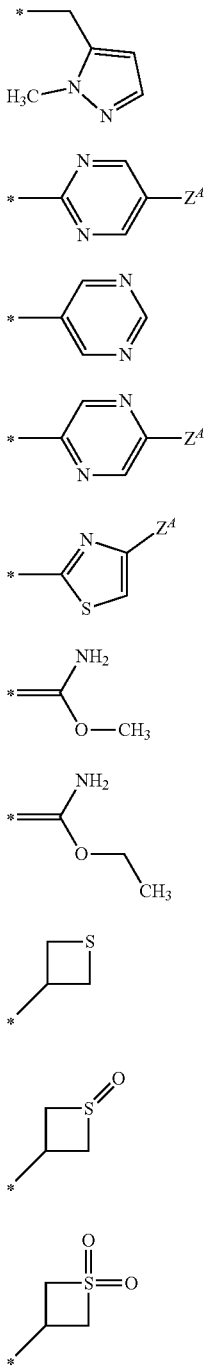
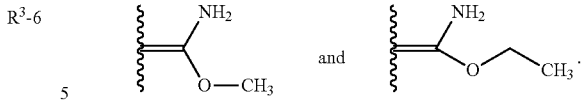

or a salt or solvate or N-oxide thereof for the manufacture of a medicament for the treatment of demodicosis in mammals, especially companion animals, especially dogs.

This invention also is directed to the isoxazoline compound as described in this application or a pharmaceutical composition comprising such isoxazoline compound for use in the treatment of generalized demodicosis in animals comprising an effective amount of an isoxazoline compound as described in this specification, and, in case of the pharmaceutical formulation, a pharmaceutically acceptable carrier.

The current invention further provides a method of controlling *Demodex* spp. mites in dogs comprising a single administration of an isoxazoline compound as described in this specification.

DETAILED DESCRIPTION OF THE INVENTION

The inventors of the current invention discovered that demodicosis of mammals can be treated by administering an effective amount of an isoxazoline compound as described in this application. It has been found that a single administration of such an isoxazoline compound resulted in a complete miticidal effect against *Demodex* spp. mites and a high efficacy against generalized demodicosis in dogs.

As it has been shown in the example, after single administration of fluralaner as Bravecto® chewable tablets to dogs, mite numbers in skin scrapings were reduced by 99.8% on Day 28 and by 100% on Days 56 and 84 after administration. Statistically significantly (P≤0.05) fewer mites were found on Days 56 and 84 on the Bravecto® treated dogs compared to the dogs that received the prior art Advocate® (imidacloprid/moxidectin) treatment on three occasions in 28 day intervals.

The prior art methods for the control of generalized demodicosis require all multiple treatments (daily or very frequent administration) of either amitraz or macrocyclic lactones such as milbemycin oxime, moxidection, ivermectin, doramectin or selamectin over a long time period.

Such multiple treatments are very burdensome as frequent handling is necessary, that require cooperation of the treated animal, which is not always the case.

A further downside of the prior art methods and reason of limited owner compliance is the high cost associated with such treatment regimens.

The prior art administration of the compounds additionally bear a high risk of side effects of such treatments because relatively high dosages of the miticidal compounds over an extended time period resulted in some cases in severe toxic side effects in treated animals, especially for ivermectin sensitive breeds of dogs such as e.g. collies.

Especially the prior art bath treatment with amitraz additionally required the owner to take special measures to avoid contact with the compound and bathing should be done in a well-ventilated area. Furthermore clipping of the dog's hair coat was required for full efficacy.

However I, in case the necessary treatment schedule is not completed, because of lack of owner compliance, the risk of a relapse of the demodicosis is very high. Another reason for wherein $Z^A$=hydrogen, halogen, cyano, halomethyl (CF$_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

treatment failure is that the used compounds had limited efficacy and some *Demodex* mites survived the treatment.

The current inventors surprisingly found that such disadvantages of the prior art can be prevented, if an isoxazoline compound as described in this application, especially fluralaner is used.

By the method of the current invention, that requires administration of an effective dosage of an isoxazoline compound according to the current invention, a premature treatment cessation by owners will be avoided.

The isoxazoline compound for use in the current invention can be described by Formula (I):

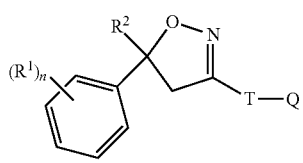

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;
Q=X—$NR^3R^4$ or a 5-membered N-heteroaryl ring, which is optionally substituted by one or more radicals $Z^A$, $Z^B$ $Z^D$;
X=$CH_2$, $CH(CH_3)$, CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

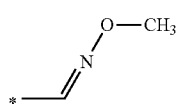 R³-1

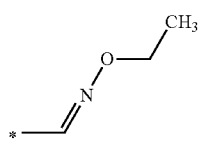 R³-2

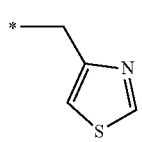 R³-3

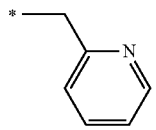 R³-4

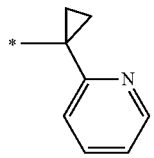 R³-5

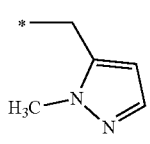 R³-6

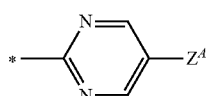 R³-7

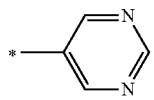 R³-8

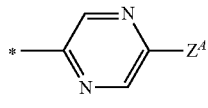 R³-9

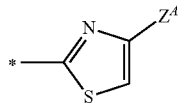 R³-10

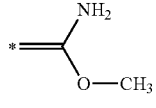 R³-11

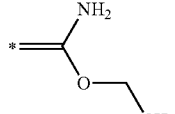 R³-12

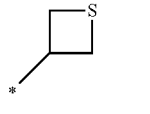 R³-13

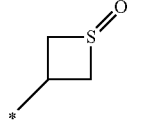 R³-14

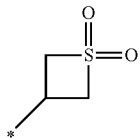
R³-15

R⁴=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or R³ and R⁴ together form a substituent selected from the group consisting of:

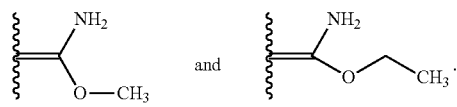

wherein $Z^A$=hydrogen, halogen, cyano, halomethyl (CF₃).

In one preferred embodiment in Formula (I) T is selected from

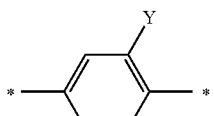
T-1

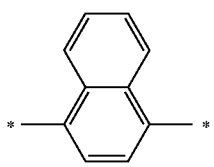
T-2

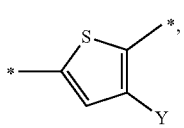
T-3

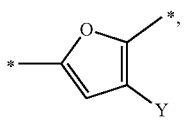
T-4

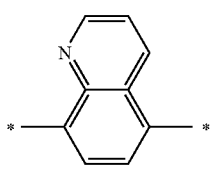
T-5

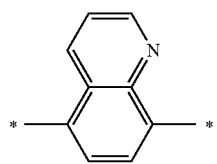
T-6

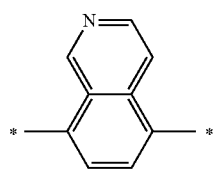
T-7

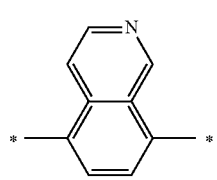
T-8

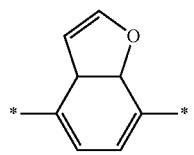
T-9

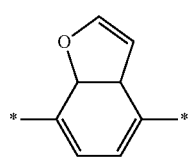
T-10

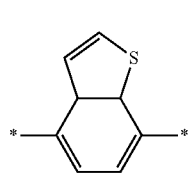
T-11

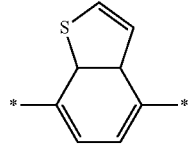
T-12

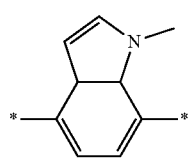
T-13

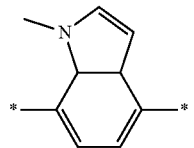
T-14

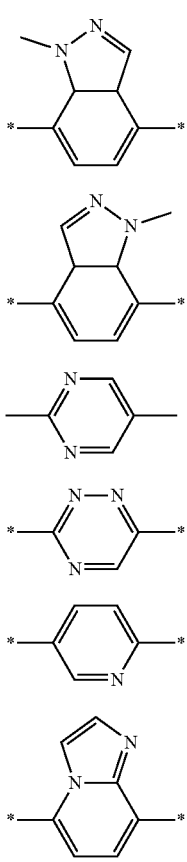
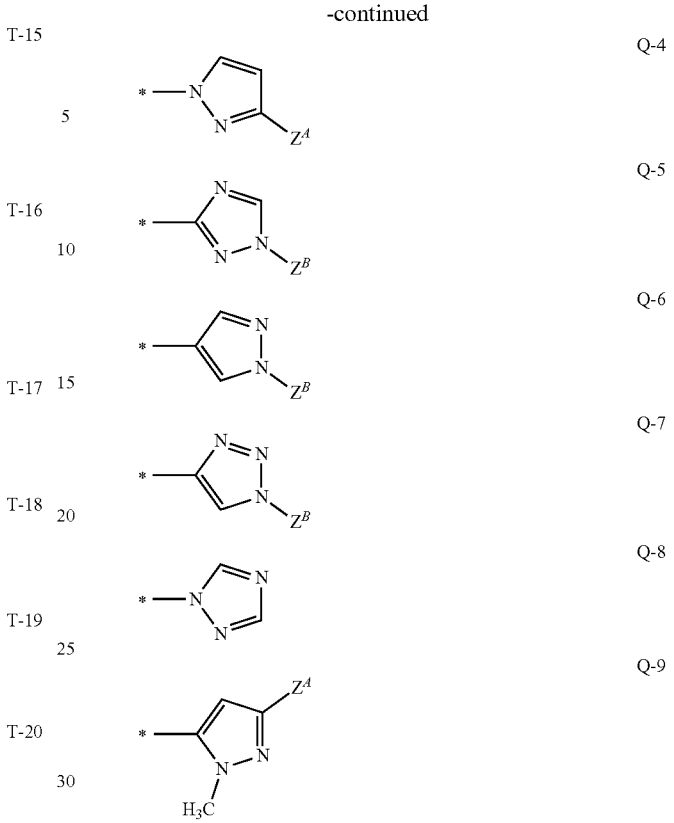
wherein in T-1, T-3 and T-4 the radical Y is hydrogen, halogen, methyl, halomethyl, ethyl, haloethyl.
In an preferred embodiment in Formula (I) Q is selected from
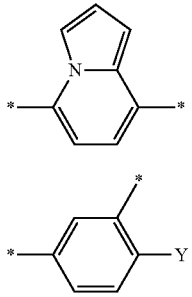
wherein $R^3$, $R^4$, X and $Z^A$ are as defined above.
$Z^B =$
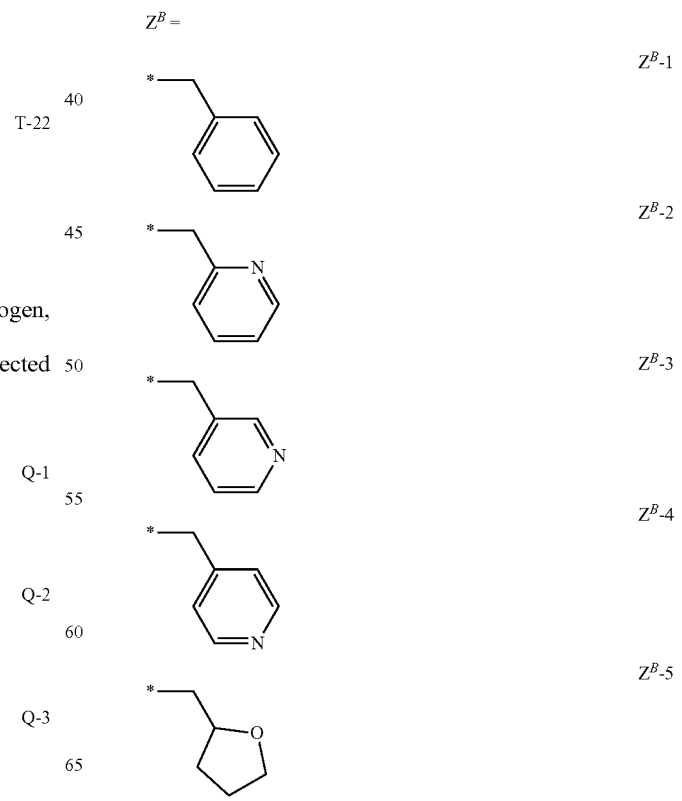

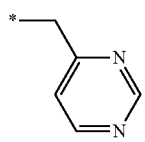

Z^B-6

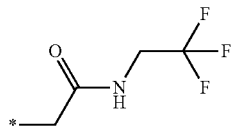

Z^B-7

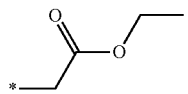

Z^B-8

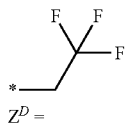

Z^B-9

Z^D =

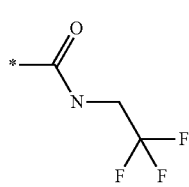

Z^D-1

Z^D-2

*—C(O)—N(CH₃)₂

Z^D-3

*—C(O)—O—CH₃

Z^D-4

Z^D-5

Z^D-6

Preferred isoxazoline compounds of Formula (I) for use in the current invention are:

| $(R^1)_n$ | $R^2$ | $R^3$ | $R^4$ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-Cl, 5Cl | CF₃ | CH₂C(O)NHCH₂CH₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-CF₃ | CF₃ | CH₂C(O)NHCH₂CH₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-CF₃, 5-Cl | CF₃ | CH₂C(O)NHCH₂CH₃ | H | T-2 | — | Q-1 | — | C(O) |
| 3-Cl, 5Cl | CF₃ | — | — | T-2 | — | Q-6 | Z^B-7 | |
| 3-Cl, 5Cl | CF₃ | — | — | T-2 | — | Q-7 | Z^B-7 | |
| 3-Cl, 5Cl | CF₃ | — | — | T-2 | — | Q-5 | Z^B-7 | |
| 3-Cl, 5Cl | CF₃ | — | — | T-2 | — | Q-2 | Z^D-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-Cl, 5Cl | CF₃ | CH₂C(O)NHCH₂CH₃ | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-CF₃, 5-CF₃ | CF₃ | CH₂C(O)NHCH₂CH₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CH₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CH₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-Cl, 5-Cl | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CH₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-CF₃, 5-CF₃ | CF₃ | CH₂C(O)NHCH₂CH₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CH₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |

-continued

| (R¹)ₙ | R² | R³ | R⁴ | T | Y | Q | Z | X |
|---|---|---|---|---|---|---|---|---|
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | CH₂C(O)NHCH₂CH₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Especially preferred isoxazoline compounds for use in the current invention are

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | Z$^B$-7 | |
| 3-Cl, 5Cl | CF₃ | — | — | T-2 | — | Q-7 | Z$^B$-7 | |
| 3-Cl, 5Cl | CF₃ | — | — | T-2 | — | Q-5 | Z$^B$-7 | |
| 3-Cl, 5Cl | CF₃ | — | — | T-2 | — | Q-2 | Z$^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred isoxazoline compound for use in the current invention has the Formula (II),

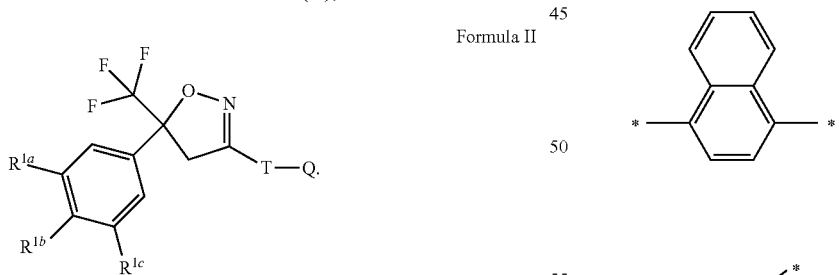

Formula II wherein
R$^{1a}$, R$^{1b}$, R$^{1c}$ are independently from each other hydrogen, Cl or CF₃, preferably R$^{1a}$ and R$^{1c}$ are Cl or CF₃ and R$^{1b}$ is hydrogen,
T is

T-1

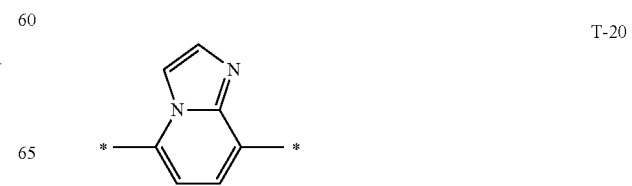

T-2

T-3

T-20

-continued

T-21

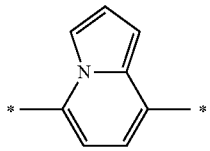

wherein

Y is methyl, bromine, Cl, F, CN or C(S)NH$_2$, and

Q is as described above.

In another preferred embodiment in Formula (II) R$^3$ is H and R$^4$ is —CH$_2$—C(O)—NH—CH$_2$—CF$_3$, —CH$_2$—C(O)—NH—CH$_2$—CH$_3$, —CH$_2$—CH$_2$—CF$_3$ or —CH$_2$—CF$_3$.

In a preferred embodiment the isoxazoline compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In another embodiment the isoxazoline compound is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the isoxazoline compound is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the isoxazoline compound is Ethanone, 1-[5'-[(5S)-5-(3,5-dichloro-4-fluorophenyl)-4,5-dihydro-5-(trifluoromethyl)-3-isoxazolyl]spiro[azetidine-3,1'(3'H)-isobenzofuran]-1-yl]-2-(methylsulfonyl)-(Sarolaner) (CAS RN-1398609-39-6).

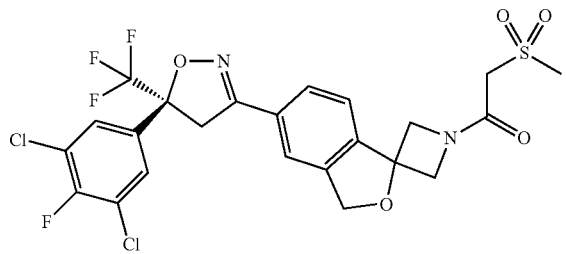 [SMILES: CS(=O)(=O)CC(=O)N1CC2(C1)OCc1cc(C3=NO[C@@](c4cc(Cl)c(F)c(Cl)c4)(C(F)(F)F)C3)ccc12]

In another embodiment the isoxazoline compound is 2-Thiophenecarboxamide, 5-((5S)-4,5-dihydro-5-(3,4,5-trichlorophenyl)-5-(trifluoromethyl)-3-isoxazolyl)-3-methyl-N-(2-oxo-2-((2,2,2-trifluoroethyl)amino)ethyl)-(INN Lotilaner) (CAS RN-1369852-71-0).

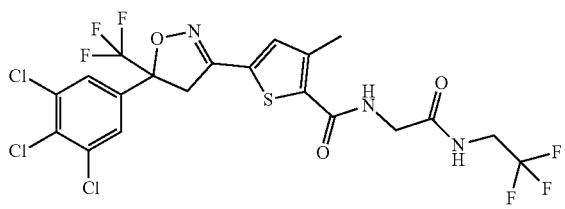 [SMILES: Cc1cc(C2=NOC(c3cc(Cl)c(Cl)c(Cl)c3)(C(F)(F)F)C2)sc1C(=O)NCC(=O)NCC(F)(F)F]

In another preferred embodiment the isoxazoline compound is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162-.

In another embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

Isoxazoline compounds and their use as antiparasitics are e.g. described in US patent application US 2007/0066617, and International Patent applications WO 2005/085216, WO 2007/079162, WO 2009/002809, WO 2009/024541, WO 2009/003075, WO 2010/070068 and WO 2010/079077.

The method (or use) of this invention comprises to use racemic mixtures, for example, equal amounts of the enantiomers of such isoxazoline compounds as described above. In addition, the method of this invention includes isoxazoline compounds that are enriched compared to the racemic mixture in an enantiomer of Formula 1. Also included are the essentially pure enantiomers of such isoxazoline compounds.

When enantiomerically enriched, one enantiomer is present in greater amounts than the other, and the extent of enrichment can be defined by an expression of enantiomeric excess ("ee"), which is defined as $(2x-1)-100\%$, where x is the mole fraction of the dominant enantiomer in the mixture (e.g., an ee of 20% corresponds to a 60:40 ratio of enantiomers). Preferably the compositions for use in the current invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Isoxazoline compounds as described above can comprise additional chiral centers. The method of this invention comprises racemic mixtures as well as enriched and essentially pure stereo configurations at these additional chiral centers.

The reference to isoxazoline compound in this specification includes enantiomers, salts and solvates as well as N-oxides thereof that can be produced by conventional methods.

By "treating" or "treat" or "treatment" is intended the application or administration of a compound or composition to an animal that has a parasitic infestation for the eradication of the parasite or the reduction of the number of parasites, infesting the animal (eliminate existing parasites). The effect can be e.g. ovicidal, larvicidal nymphicidal, or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate.

An "effective amount," is the amount or quantity of an isoxazoline compound as described above that is required to treat Demodex spp. infestations of animals, i.e. to alleviate or reduce parasite numbers on an animal, and/or to inhibit the development of parasite infections on an animal, in whole or in part.

This amount is readily determined by observation or detection of the parasite numbers on the animal both before and after administering an isoxazoline compound as described above to such animals, e.g. the parasite count is reduced, after a first administration, by 5% to about 100%, preferably more than 50%, more than 70%, more than 90%, more than 95%, more than 99%, especially 100%.

Preferably the effective amount results in microscopical cure, i.e. that no *Demodex* spp. mites are present in the deep skin scrapings of affected skin (preferably three to five scrapings of most severely affected areas), preferably taken at several time points.

The effective amount for treatment of generalized demodicosis additionally leads to diminishing or resolution of clinical signs of demodicosis as described in this application.

Typically effective (dosage) amount of isoxazoline compounds, are between 1 mg/kg bodyweight of the treated animal and 50 mg/kg bodyweight, or 5 mg/kg bodyweight to 45 mg/kg bw, or 10 mg/kg bw to 40 mg/kg bw, or 20 to 30 mg/kg bw. In one embodiment the effective dosage is 25 mg/kg bodyweight.

In one embodiment a single dose of an effective amount of the isoxazoline compound is administered to a mammal, especially dog, that is infested with *Demodex* spp. mites.

In one embodiment a single dose of an effective amount of the isoxazoline compound is administered to a dog that has been diagnosed with a generalized canine demodicosis.

In another embodiment two doses of an effective amount of the isoxazoline compound are administered to a mammal, especially dog, that is infested with *Demodex* spp. mites.

In one embodiment a two doses of an effective amount of the isoxazoline compound are administered to a dog that has been diagnosed with a generalized canine demodicosis.

In another embodiment three doses of an effective amount of the isoxazoline compound are administered to a mammal, especially dog, that is infested with *Demodex* spp. mites.

In one embodiment a three doses of an effective amount of the isoxazoline compound are administered to a dog that has been diagnosed with a generalized canine demodicosis.

Preferred is the systemic administration of the isoxazoline compounds. "Systemic administration" is an administration at a site remote from a site wherein at least a portion of the target parasites reside. With systemic administration, at least a portion of the isoxazoline compound reaches the target parasite via the animal recipient's bloodstream, other body fluids (lymph fluids), and/or tissues (e.g., skin or fat tissue). This is in contrast to "contact activity" were the surface of the parasite body is directly exposed to the isoxazoline compound. Typically, the parasite ingests the systemic administered isoxazoline along with the animal recipient's blood, other body fluids, and/or tissue. Systemic administration may be achieved in several forms, e.g. oral, parenteral or via topical administration wherein the isoxazoline compound is transdermally absorbed.

In some embodiments, the isoxazoline compound is systemically administered via an oral route in a unit dosage form, such as, for example, a soft or hard capsule, a pill, a powder, granules, a tablet (e.g., a chewable tablet), a paste, a solution, a suspension (aqueous or non-aqueous), an emulsion (oil-in-water or water-in-oil), an elixir, a syrup, a bolus, a drench, or via the animal recipient's feed or drinking water. Alternatively oral administration can be performed via the animal recipient's feed or drinking water e.g. it may be intimately dispersed in the animal recipient's regular feed, used as a top dressing, or in the form of pellets or liquid that is added to the finished feed.

One form of oral administration is a dosage form, e.g. a chewable composition, such as a chewable tablet. Examples of chewable tablets comprising isoxazoline compounds of formula (I) were described in WO2013/150052 and WO2013/150055. The composition of the chewable tablets that is disclosed in the examples of these documents is incorporated by reference. Alternative chewable tablets are described in WO2013/119442.

Oral veterinary compositions in the form of a "chewable tablet", sometimes referred to as "soft chewable compositions" or "soft chew", are usually convenient to administer to certain animals, particularly cats and dogs, preferably dogs, and may be used effectively to dose veterinary medicine to these animals.

A "Chewable tablet", "Soft chew" or "Soft chewable pharmaceutical product" is intended to mean a pharmaceutical unit dose that is solid at room temperature and that is after oral administration soft to chew by the animal and which is functionally chewy because the product has some plastic texture during the process of mastication in the mouth. Such soft chews have a softness that is similar to a cooked ground meat petty. The chewable tablet or soft chew comprises a carrier and other non-active ingredients.

The isoxazoline compound alternatively (or additionally) may be systemically administered topically using a transdermal formulation (i.e., a formulation that passes through the skin). Alternatively (or additionally), the composition may be systemically administered topically via the mucosa. The isoxazoline composition alternatively (or additionally) may be systemically administered parenterally, such as via intramuscular injection, intravenous injection, subcutaneous injection, implant (e.g., subcutaneous implant), infusion, bolus, etc.

The animals may receive an isoxazoline compound as defined earlier once, two times or three times until the *Demodex* mite infestation is controlled and the generalized demodicosis is successfully treated. One treatment provides effectiveness against *Demodex* spp. mites for at least 4 weeks, 8 weeks, 12 weeks, 16 weeks or 20 weeks, or 24 weeks.

In general the isoxazoline compound can be administered to all species of animals that have *Demodex* spp. infestation or require treatment of a demodicosis.

The recipient of the product may be a livestock animal, e.g. sheep, cattle, pig, goat; or a companion animal, e.g. dog, cat, or horse. Especially preferred is the use in companion animals, e.g. dogs or cats, especially dogs.

*Demodex* spp. mites that can be controlled by the use according to the current invention are e.g. *Demodex canis, Demodex injai, Demodex cornei, Demodex. cati, Demodex gatoi, Demodex bovis, Demodex ovis, Demodex caprae, Demodex aries*.

A "*Demodex* mite infestation" refers to the presence of parasites in numbers that pose a risk of r harm to animals.

By using the isoxazoline compounds as described in this application disadvantages of the prior art can be avoided, because a single (or maximal two or three times, depending on the isoxazoline compound used) administration of the compound would be necessary to achieve the desired effect.

Demodicosis is diagnosed by clinical evaluation and deep skin scrapings that is analysed using a microscope for mites present. Demodicosis is considered generalized when five or more areas of localized disease are observed, or pododemodicosis is observed on two or more feet, or when an entire body region is involved. Demodicosis can also be categorized as either juvenile (dogs up to 18 months of age), adult onset (dogs generally older than four years of age with no previous history of disease), or chronic generalized (persisting disease for at least six months).

Depending on the specific isoxazoline compound used, the administration allows to completely inhibit or kill the *Demodex* spp. mites present on the animal that cause the demodicosis. Preferably, microscopic cure, i.e. multiple skin scrapings without any *Demodex* mites (eggs, larvae, nymphs and adults) is obtained by the administration of the isoxazoline compound. Preferably only one administration is necessary for microscopic cure.

The administration of the isoxazoline compound, e.g. fluralaner is able to reduce the clinical signs of the demodicosis, and preferably at least one of the dermatological signs, e.g. the skin lesions, such as erythema, casts, pustules, scales and crusts, exudation, ulceration and hair loss up to alopecia is reduced significantly compared to the situation before treatment or without treatment.

The administration of the isoxazoline compound, e.g. fluralaner is able to cure together with a symptomatic therapy (e.g. antibiotics or antiseptics) the appearance of systemic symptoms such as generalized lymphadenopathy, lethargy, and fever.

The treatment of canine generalized demodicosis in most cases requires adjunctive therapy. In addition to the effective miticidal therapy by the isoxazoline compounds according to the current invention, treatment of concurrent bacterial skin infection, internal parasites and existing underlying systemic diseases might be undertaken for successful treatment.

The isoxazoline compound as described in this application can be used concurrently with suitable antibiotics in order to control the secondary bacterial skin infection pyoderma that is usually associated with generalized demodicosis. Superficial pyoderma can be treated with oral antibiotics or topical antibiotics. In certain cases topical treatment with benzoyl peroxide or chlorhexidine-based shampoos will be useful to control the bacterial secondary infections.

EXAMPLE

Efficacy of orally administered fluralaner (as Bravecto® chewable tablets 13.64% fluralaner) compared to topically applied Advocate® (10-% imidacloprid/2.5% moxidectin) against generalized demodicosis in dogs.

Methods

Study Set-Up

The study was designed as a parallel group, blinded, randomized, single centre, and positive controlled efficacy study. Bravecto® administered as chewable tablets on a single occasion was the test product and Advocate®, administered three times at 28 day intervals (according to the product label) was included as a positive control.

The test system was the individual dog. Dogs with clinical signs of generalized demodicosis, e.g. erythema, hair loss, comedones, follicular casts and crusts were enrolled, with consent from their owners, in the study and were returned to their owners on completion of the animal phase.

Dogs included in the study were mostly mongrels and of both sexes, older than 12 months, weighed between 3.5 and 13.7 kg, and except for clinical signs of generalized demodicosis, the dogs were healthy and as far as could be determined the dogs had not been treated with a glucocorticoid or any product with a miticidal effect for at least 12 weeks prior to inclusion. Additional requirements for inclusion were that deep skin scrapings performed before treatment had to be positive for *Demodex* spp. mites.

Sixteen dogs (7 male and 9 female), ranked within sex in descending order of individual pre-treatment mite counts were included in the study and allocated to two equal groups. Each dog was housed individually for the duration of the study in an indoor/outdoor run, without contact between animals, and was fed once a day according to the food manufacturer's recommendations. Potable municipal water was available ad libitum.

Each dog was acclimatized to the housing and maintenance conditions for at least 14 days before treatment. As a precautionary measure all dogs were treated subcutaneously with an antibiotic (cefovecin), appropriate for the treatment of pyoderma on Days −14, −1, 13 and 27. Additionally, on Days −14 and 27, deep skin biopsies were taken from each dog after sedation. The biopsies indicated that exudative pyoderma was present in two dogs in each group on Day −14 and that it had cleared by Day 27. Chronic dermatitis, epidermal acanthosis and hyperkeratosis was present and unchanged in all dogs on both occasions. No inflammatory cells or bacteria were observed in the Day 27 biopsies and antimicrobial therapy was discontinued. Twice during acclimatization (Day −14 and Day −1) and on Days 27/28, 56 and 84 after treatment each dog was clinically examined by a veterinarian.

The dogs were weighed on a calibrated and verified electronic scale on Days −2, 13, 27, 41, 55, 69 and 84 for dose calculation for treatment, for the use of sedatives for skin scrapings and to document the body weight during the study period. General health observations were performed daily throughout the complete study period.

Treatment

On Day 0, dogs of one group were treated once orally with Bravecto® chewable tablets, based on the dog's individual body weight, to achieve a minimum dose of 25 mg/kg body weight and an efficacy over 12 weeks following treatment. The chewable tablet(s) were administered 20 (±10) minutes after food had been offered by placement in the back of the oral cavity over the tongue to initiate swallowing.

Also on Day 0, commercially available Advocate® was administered topically to the other group of dogs (positive controls) according to the product label. Due to the 28 days efficacy duration of Advocate®, these dogs were re-treated on Day 28 and 56. With the dog in a standing position, the coat was parted until the skin was visible and the Advocate® was administered directly onto the skin.

Both treated groups were observed prior to treatment and again hourly for four hours after treatment of the last animal, for possible adverse events. Personnel performing the post-treatment observations were blinded with respect to the treatment.

Mite Assessments

Deep skin scrapings (~4 cm$^2$) were made from five sites on each dog on Days −4, 28, 56 and 84 and were examined under a stereomicroscope for the presence of *Demodex* spp. mites. Skin scrapings of the dogs treated with Advocate® were performed on Day 28 and Day 56, before the second or third treatment was applied, respectively. The same sites and/or sites of new lesions were scraped at each subsequent examination.

The clinical signs and the extent of demodectic lesions on each dog were assessed on the days when skin scrapings were made, and recorded on a standardised form. The following parameters were assessed and sketched on a silhouette (left and right hand side) for each dog: body areas exhibiting erythema; body areas covered by casts, scales and crusts; body areas with hair loss (1=slight thinning of hair; 2=conspicuous hair loss; 3=no hair). Colour photographs illustrating the extent of lesions and their resolution, were taken of each dog on Day −4 and subsequently at approximately monthly intervals up to Day 84 after treatment. A semi-quantitative assessment of hair re-growth was performed, comparing hair coat before and after the 12 weeks study duration.

Efficacy Evaluation

The primary assessment variable in the study was the decrease in number of mites counted in skin scrapings (immature and adult live mites combined) following treatment.

Efficacy was calculated using geometric means with Abbott's formula:

Efficacy (%)=($M$pre−$M$post)/$M$pre×100 where Mpre was the mean number of pre-treatment mite counts, and Mpost the mean number of post-treatment mite counts.

Additionally, the groups were compared using an ANOVA (Proc GLM procedure in SAS) with a treatment effect after a logarithmic transformation on the mite (count+1) data.

One dog treated with Advocate® was removed from the study on Day 59 due to malignant lymphoma. The results pertaining to this dog until Day 56, before its exclusion from the study on Day 59, have been included with those of the other dogs in the group treated with Advocate®.

Results

No adverse event considered to be related to oral treatment with Bravecto® chewable tablets or topical treatment with Advocate® was observed in any dog.

Treatment with Bravecto® chewable tablets resulted in a reduction in the mean mite number present in skin scrapings of 99.8% on Day28, and of 100% on Days 56 and 84 after treatment. The treatment with Advocate® resulted in a reduction in the mean mite number present in skin scrapings of 98.0% on Day 28, of 96.4% on Day 56, and of 94.7% on Day 84. Statistically significantly ($P \leq 0.05$) fewer mites were found on the Bravecto® treated dogs compared to Advocate® treated dogs (Table 1).

TABLE 1

Geometric mean reductions in *Demodex* spp. mite counts of dogs treated once orally with Bravecto ® or topically on three occasions at 28 day intervals with Advocate ®

| Study Days | Study groups | Bravecto ® | Advocate ® | p-value |
|---|---|---|---|---|
| −4 | Mean$^a$ mite counts (n) | 447.0 | 509.4/478.6 $^b$ | |
|  | Count range (n) | 41-1740 | 79-2724 | |
| 28 | Mean$^a$ mite counts (n) | 0.8 | 10.0 | |
|  | Count range (n) | 0-14 | 0-496 | |
|  | Efficacy (%) | 99.8 | 98.0 | 0.0917 |
| 56 | Mean$^a$ mite counts (n) | 0.0 | 18.5 | |
|  | Count range (n) | Na$^c$ | 0-115 | |
|  | Efficacy (%) | 100.0 | 96.4 | <0.0001 |
| 84 | Mean$^a$ mite counts (n) | 0.0 | 25.6 | |
|  | Count range (n) | Na$^c$ | 0-286 | |
|  | Efficacy (%) | 100.0 | 94.7 | 0.0020 |

$^a$Geometric mean
$^b$ Mite counts calculated without one dog, which was euthanized on Day 59
$^c$Not applicable The prevalence of erythematous patches on the dogs treated once orally with Bravecto® chewable tablets was reduced from 62.5% of the dogs on Day −4 prior to treatment to 12.5% of the dogs 12 weeks following initiation of treatment.

The prevalence of crusts, casts or scales was reduced from 100% prior to treatment to 12.5% 12 weeks following initiation of treatment.

In comparison, the prevalence of erythematous patches on dogs treated three times at a 28 days interval with Advocate® was reduced from 87.5% to 0% and the prevalence of crusts, casts and scales was reduced from 100% to 42.9% (Table 2).

TABLE 2

Reduction in the prevalence of dermatologic changes in dogs with generalized demodicosis after treatment with either Bravecto ® or Advocate ®

Bravecto ®: prevalence of lesions on days before and after treatment$^a$
(number of dogs/number of dogs per group)

| Clinical Symptom | Day −4 | Day 28 | Day 56 | Day 84 |
|---|---|---|---|---|
| Erythematous patches | 62.5% (5/8) | 37.5% (3/8) | 12.5% (1/8) | 12.5% (1/8) |
| Crusts, casts or scales | 100% (8/8) | 62.5% (5/8) | 62.5% (5/8) | 12.5% (1/8) |

TABLE 2-continued

Reduction in the prevalence of dermatologic changes in dogs with generalized demodicosis after treatment with either Bravecto ® or Advocate ®

| Advocate ®: prevalence of lesions on days before and after initial treatment[b] (number of dogs/number of dogs per group) | | | | |
|---|---|---|---|---|
| Clinical Symptom | Day −4 | Day 28 | Day 56 | Day 84 |
| Erythematous patches | 87.5% (7/8) | 50% (4/8) | 0% (0/8) | 0% (0/7)[c] |
| Crusts, casts or scales | 100% (8/8) | 100% (8/8) | 37.5% (3/8) | 42.9% (3/7)[c] |

[a]Dogs were treated once orally on Day 0
[b]Dogs were treated topically on Day 0, on Day 28 and again on Day 56. Skin assessments were performed before treatment.
[c]Mite counts calculated without one dog, which was euthanized on Day 59.

Hair re-growth compared to the proportion of the body area covered by hair prior to treatment is summarized in Table 3. By Days 56 and 84 after initiation of treatment, hair re-growth on the majority of dogs in both groups exceeded the hair-coat of the dogs by 90% compared with the pre-treatment assessment.

TABLE 3

Hair re-growth on dogs with generalized demodectic mange after treatment with Bravecto ® or Advocate ®

| | Hair re-growth score: frequency of occurrence | | | | | |
|---|---|---|---|---|---|---|
| | Bravecto ®[a] (number of dogs/number of dogs per group) | | | Advocate ®[b] (number of dogs/number of dogs per group) | | |
| Study day | 1 (0-50%) | 2 (50-90%) | 3 (>90%) | 1 (0-50%) | 2 (50-90%) | 3 (>90%) |
| 28 | 3/8 | 1/8 | 4/8 | 6/8 | 1/8 | 1/8 |
| 56 | 0/8 | 1/8 | 7/8 | 0/8 | 1/8 | 7/8 |
| 84 | 0/8 | 1/8 | 7/8 | 0/7[c] | 1/7[c] | 6/7[c] |

[a] Dogs were treated once orally on Day 0
[b] Dogs were treated topically on Day 0, on Day 28 and again on Day 56. Skin assessments were performed before treatment.
[c]Mite counts calculated without one dog, which was euthanized on Day 59.

The body weight of every dog increased similarly in both groups during the study period.

CONCLUSIONS

Single oral administration of Bravecto® (13.64% fluralaner) chewable tablets is highly effective against generalized demodicosis, with no mites detectable at 56 and 84 days following treatment. In comparison, Advocate® (10% imidacloprid/2.5% moxidectin) administered three times at 28 day intervals, is also highly effective against generalized demodicosis, but most dogs still harboured mites at all assessment time points. Both treatments resulted in a marked reduction of skin lesions and increase of hair-growth 12 weeks after the initial treatment.

The invention claimed is:

1. A Method of treating generalized demodicosis in a dog that had been diagnosed with a generalized canine demodicosis comprising administering a composition comprising an effective amount of an isoxazoline compound of Formula (II)

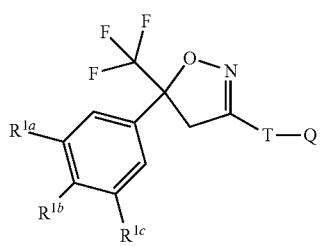

Formula II wherein
$R^{1a}$, $R^{1b}$, $R^{1c}$ are independently from each other hydrogen, Cl or $CF_3$,
T=

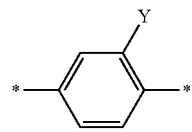

T-1

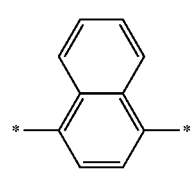

T-2

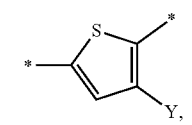

T-3

Y=methyl, halomethyl, halogen, CN, $NO_2$, or $NH_2$—C=S,
Q=X—$NR^3R^4$;
X=$CH_2$, $CH(CH_3)$, CH(CN), CO, or CS,
$R^3$=hydrogen;
$R^4$=hydrogen, ethyl, methoxymethyl, halomethoxymethyl, ethoxymethyl, haloethoxymethyl, propoxymethyl, methylcarbonyl, ethyl carbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, haloethylaminocarbonylethyl, —CH₂—C(O)—NH—CH₂—CF₃, —CH₂—C(O)—NH—CH₂—CH₃, —CH₂—CH₂—CF₃ or —CH₂—CF₃;

or a salt or solvate or N oxide thereof and a pharmaceutically acceptable carrier, wherein the composition is administered once, twice or three times, wherein the treatment results in microscopical cure.

2. The method according to claim 1 comprising a single administration of the isoxazoline compound to the dog.

3. The method according to claim 1 wherein the isoxazoline compound is administered to the dog orally.

4. The method according to claim 1 wherein the isoxazoline compound is administered to the dog topically.

5. The method according to claim 1 wherein the isoxazoline compound is administered to the dog parenterally by injection.

6. The method according to claim 1, wherein the amount of the isoxazoline compound is effective to reduce the parasite count by 100%.

7. A method of treating generalized demodicosis in a dog that had been diagnosed with a generalized canine demodicosis comprising administering a composition comprising an effective amount of fluralaner or a salt or solvate or N oxide thereof and a pharmaceutically acceptable carrier, wherein the composition is administered once, twice or three times and wherein the treatment results in microscopical cure.

8. The method according to claim 7 comprising a single administration of 10-40 mg/kg bodyweight of fluralaner to the dog.

9. The method according to claim 7 comprising a single administration of the fluralaner to the dog.

10. The method according to claim 7 wherein the fluralaner is administered to the dog orally.

11. The method according to claim 7 wherein the fluralaner is administered to the dog topically.

12. The method according to claim 7 wherein the fluralaner is administered to the dog parenterally by injection.

13. The method according to claim 7, wherein the amount of the fluralaner is effective to reduce the parasite count by 100%.

14. A method of treating generalized demodicosis in a dog that had been diagnosed with a generalized canine demodicosis comprising administering a composition comprising an effective amount of afoxolaner or a salt or solvate or N oxide thereof and a pharmaceutically acceptable carrier, wherein the composition is administered once, twice or three times and wherein the treatment results in microscopical cure.

15. The method according to claim 14 comprising a double or triple administration of the afoxolaner to the dog.

16. The method according to claim 14 wherein the afoxolaner is administered to the dog orally.

17. The method according to claim 14 wherein the afoxolaner is administered to the dog topically.

18. The method according to claim 14 wherein the afoxolaner is administered to the dog parenterally by injection.

19. A method of treating generalized demodicosis in a dog that had been diagnosed with a generalized canine demodicosis comprising administering a composition comprising an effective amount of sarolaner or a salt or solvate or N oxide thereof and a pharmaceutically acceptable carrier, wherein the composition is administered once, twice or three times and wherein the treatment results in microscopical cure.

20. The method according to claim 19 comprising a double or a triple administration of the sarolaner to the dog.

21. The method according to claim 19 wherein the sarolaner is administered to the dog orally.

22. The method according to claim 19 wherein the sarolaner is administered to the dog topically.

23. The method according to claim 19 wherein the sarolaner is administered to the dog parenterally by injection.

24. A method of treating generalized demodicosis in a dog that had been diagnosed with a generalized canine demodicosis comprising administering a composition comprising an effective amount of lotilaner or a salt or solvate or N oxide thereof and a pharmaceutically acceptable carrier, wherein the composition is administered once, twice or three times and wherein the treatment results in microscopical cure.

25. The method according to claim 24 comprising a double or a triple administration of the lotilaner to the dog.

26. The method according to claim 24 wherein the lotilaner is administered to the dog orally.

27. The method according to claim 24 wherein the lotilaner is administered to the dog topically.

28. The method according to claim 24 wherein the lotilaner is administered to the dog parenterally by injection.

* * * * *